(12) United States Patent
Banet et al.

(10) Patent No.: US 7,396,330 B2
(45) Date of Patent: Jul. 8, 2008

(54) WIRELESS, INTERNET-BASED MEDICAL-DIAGNOSTIC SYSTEM

(75) Inventors: Matthew Banet, Del Mar, CA (US); Randon Schultz, Venice, CA (US); Robert Murad, San Diego, CA (US)

(73) Assignee: Triage Data Networks, Del Mar, CA (US)

( * ) Notice: Subject to any disclaimer, the term of this patent is extended or adjusted under 35 U.S.C. 154(b) by 481 days.

(21) Appl. No.: 10/752,198

(22) Filed: Jan. 6, 2004

(65) Prior Publication Data

US 2005/0010087 A1   Jan. 13, 2005

Related U.S. Application Data

(60) Provisional application No. 60/438,442, filed on Jan. 7, 2003.

(51) Int. Cl.
*A61B 5/00* (2006.01)

(52) U.S. Cl. .................. 600/300; 128/903

(58) Field of Classification Search ......... 600/300–301; 128/903–905, 920; 705/1–4; 340/539.1, 340/573
See application file for complete search history.

(56) References Cited

U.S. PATENT DOCUMENTS

| | | | |
|---|---|---|---|
| 5,778,882 A | 7/1998 | Raymond et al. | |
| 5,897,493 A | 4/1999 | Brown | |
| 5,997,476 A | 12/1999 | Brown | |
| 6,024,699 A * | 2/2000 | Surwit et al. | 600/300 |
| 6,095,985 A | 8/2000 | Raymond et al. | |
| 6,101,478 A | 8/2000 | Brown | |
| 6,168,563 B1 | 1/2001 | Brown | |
| 6,282,441 B1 | 8/2001 | Raymond et al. | |
| 6,368,273 B1 | 4/2002 | Brown | |
| 6,443,890 B1 * | 9/2002 | Schulze et al. | 600/300 |
| 6,579,231 B1 * | 6/2003 | Phipps | 600/300 |
| 6,790,178 B1 * | 9/2004 | Mault et al. | 600/300 |

* cited by examiner

*Primary Examiner*—Max F. Hindenburg
*Assistant Examiner*—Michael C Astorino
(74) *Attorney, Agent, or Firm*—Wilmer Cutler Pickering Hale & Dorr LLP

(57) ABSTRACT

A system for monitoring a patient's vital signs that features a vital-sign monitor including sensors for measuring from the patient at least one of the following vital-sign data: $O_2$ saturation, blood pressure, electro-cardiogram, respirator rate, and blood glucose level. The system also includes a global positioning system that determines location-based data. A wireless transmitter, in electrical contact with the vital-sign monitor and global positioning system, receives the vital-sign and location-based data and wirelessly transmits these data through a conventional wireless network. A gateway software piece receives and processes the data from the wireless network and stores these data in a computer memory associated with a database software piece. The system also includes an Internet-based user interface that displays the vital sign data for both individual patients and care-providers.

28 Claims, 8 Drawing Sheets

WIRELESS, INTERNET-BASED MEDICAL-DIAGNOSTIC SYSTEM

This application claims the benefit of U.S. Provisional Application No. 60/438,442, filed Jan. 7, 2003.

FIELD OF THE INVENTION

The present invention features a wireless, internet-based system for diagnosing a patient.

BACKGROUND OF THE INVENTION

Medical professionals use a variety of medical devices to measure a patient's vital signs during a routine checkup. Such devices can measure, for example, blood pressure, blood oxygen saturation (called $O_2$ saturation), electro-cardiograms, heart rate, respiratory rate, and blood glucose level. A sphygmomanometer measures blood pressure with an inflatable cuff and sensing electronics that determine the patient's systolic and diastolic blood pressure. Another medical device, called a pulse oximeter, clips to the patient's finger and measures the percentage of haemoglobin that is saturated with oxygen. To make this measurement, the pulse oximeter includes separate light sources (e.g. diode lasers or light-emitting diodes) that emit radiation at two different wavelengths (typically 650 nm and 805 nm). Haemoglobin in the blood partly absorbs the light to a degree that depends on whether it is saturated or desaturated with oxygen. A calculator in the oximeter calculates the absorption at the two wavelengths and computes the proportion of haemoglobin that is oxygenated. The data are dependant on a pulsatile flow of blood and are typically plotted as a waveform that the calculator additionally analyzes to determine the patient's heart rate.

An electrocardiography measurement device measures a patient's electrocardiogram (ECG) with at least three conductive electrodes that attach to the patient. The electrodes detect time-dependent electrical impulses generated by the patient's beating heart. The measurement device also includes software that analyzes the impulses to determine a time-dependent waveform from which the patient's heart rate and cardiac response are calculated. The same electrodes used to measure an ECG can also include transducers or accelerometers that detect a patient's respiratory (i.e. breathing) rate.

Diabetic patients typically monitor their blood glucose level using a simple device called a glucometer. For these measurements, the patient draws a small sample of blood (by pricking a finger, for example) and applies this to a test strip. The patient then inserts the test strip into the glucometer, which includes an electrical system to determine the electrical properties of the blood. Software in the glucometer uses these properties to determine the patient's glucose level.

In typical applications, data indicating blood pressure, $O_2$ saturation, ECG, heart rate, and respiratory rate are measured during a patient's appointment with a medical professional, such as a doctor, nurse, or certified diabetic educator. Once measured, the medical professional manually records these data in either a written or electronic file. Appointments typically take place a few times each year. And in some cases patients experience 'white coat syndrome' where anxiety during the appointment affects the vital signs that are measured. For example, white coat syndrome can elevate a patient's heart rate and blood pressure; this, in turn, can lead to an inaccurate diagnoses.

A diabetic patient will typically use a glucometer to measure their blood glucose levels several times each day, typically before and after meals. The patient may record the data in a logbook, which is then reviewed during at home or during a medical appointment. Some glucometers additionally include both electronic memory and a serial interface. In this case a personal computer equipped with the appropriate software and serial cable can download data from the glucometer and store it electronically in a file. The software may also include graphical capabilities that can, for example, plot data so that the patient can make a relatively sophisticated analysis of their blood glucose level.

Some medical devices for measuring the above-mentioned vital signs include systems for transmitting data from a remote site, such as the patient's home, to a central database. These systems can include a conventional computer modem that transmits data through a telephone line to the database. Or alternatively they can include a wireless transmitter, such as a cellular telephone or a radio modem, which wirelessly transmits the data through a wireless network.

BRIEF SUMMARY OF THE INVENTION

In general, in one aspect, the invention features a wireless, internet-based medical device for remotely monitoring a patient. Specifically, it measures data characterizing a patient's vital signs, wirelessly transmits these data through a wireless network to an internet-accessible software piece, analyzes the data, and then avails the analyzed data over a web site hosted on the internet. A medical professional, such as a registered nurse working in a call center, can view and analyze these data in real-time to accurately diagnose the patient. In this way a thorough medical 'appointment' can be conducted over the telephone or Internet while the patient remains at home. A single medical professional can monitor hundreds of patients, each in separate remote site, using the Internet.

In general, in another aspect, the invention features a system for monitoring a patient's vital signs that includes a vital-sign monitor. The monitor includes sensors for measuring from the patient at least one of the following vital-sign data: $O_2$ saturation, blood pressure, ECG, respiratory rate, and blood glucose level. The system also includes a wireless transmitter, in electrical contact with the vital-sign monitor, that receives the vital-sign data and wirelessly transmits these data through a conventional wireless network. A gateway software piece then receives and processes the vital-sign data from the wireless network and stores these data in a database associated with a database software piece. The system also includes separate Internet-based user interfaces that display the vital sign data for: 1) individual users (e.g., a 'patient interface'); and 2) groups of users (e.g., a 'care-provider interface') associated with a care-provider.

In one embodiment, the Internet-based user interface features a login functionality that analyzes input information (e.g., a login and password) and in response renders either the first or second interface.

The care-provider interface typically includes a numerical table that displays the vital-sign data associated with the plurality of patients (e.g., users). This interface can also display an 'alert' message associated with a user. For example, alert messages can be text messages with associated graphics that indicate a patient's status. To generate such alert messages, the system can include an application software piece that processes vital-sign data. To generate the alert message, the software piece can be an algorithm that compares the vital-sign data to a pre-determined level. Or the software piece can process multiple vital-sign data, or the patient's gender or age, to generate the alert message.

In other embodiments, the system further includes a first software component that transmits an electronic file, and the vital-sign monitor includes a second software component that receives the electronic file. In this case the Internet-based user interface includes a web page that sends an email, electronic message, or database-generated report, such as pre-determined file stored in the database, to a patient. The messages can be automatically sent following analysis of the vital-sign data.

In some embodiments, the first software component is configured to transmit data formatted in an XML-based format (e.g. an XML document). The XML-based format can be compatible with a second Internet-based software system. In particular, the XML-based format can integrate with a Web Services software system so that information can be sent from one web-based application to another. In other embodiments, the vital-sign monitor further includes a display that displays an email or electronic message received from the Internet. The second software component can be configured to receive and process wirelessly transmitted computer code. For example, the computer code can update the vital-sign monitor's existing computer code. Or it can function to load a schema into the monitor's memory, or modify its transmission properties (e.g., the frequency at which it transmits data, or the type of data that are transmitted).

In general, in still another aspect, the invention features a system for monitoring a patient that includes a vital-sign monitor integrated into a unit that is head-worn, wrist-worn or finger-worn. The monitor can include both wrist-worn and finger-worn components. The vital-sign monitor includes a sensor that measures data characterizing $O_2$ saturation from the patient. Typically for the head-worn unit the data are measured from a region on the patient's head. The system also includes a global positioning system that determines location-based data. A processor, in wired or unwired electrical contact with the vital-sign monitor and the global positioning system, receives and processes the $O_2$ saturation and location-based data to determine the patient's vital signs and location. The head-worn unit can also include a display or an earpiece using a text-to-speech controller to display or describe the vital signs. Such a device, for example, could be used during exercise (e.g., jogging).

In an embodiment, the head-worn unit is a pair of eyeglasses or sunglasses that features an optical sensor measuring $O_2$ saturation from the patient's earlobe. The display is integrated into a transparent portion of the eyeglasses, or the earpiece can be integrated into the frames near the patient's ear. In either case, the patient is made aware of their $O_2$ saturation and location-based data, and derivatives thereof, during exercise. The finger-worn unit can take the form of a finger ring.

In general, in still yet another aspect, the invention features a system for monitoring a patient that includes a blood-pressure monitor that measures $O_2$ saturation data from the patient. A processor, in wired or unwired electrical contact with the monitor, receives and processes the $O_2$ saturation data to determine blood pressure. A wireless transmitter receives the blood pressure data and transmits this information through a wireless network.

In general, in another aspect, the invention features a patient monitoring system that includes a blood-pressure monitor integrated into a finger or wrist-worn unit comprising a sensor that measures data characterizing $O_2$ saturation and blood pressure from the patient. A processor, in wired or unwired electrical contact with the monitor, receives and processes the $O_2$ saturation and blood pressure data. And a wireless transmitter receives the $O_2$ saturation and blood pressure data from the processor and transmits these data through a wireless network.

In the above-described systems, the term 'wireless network' refers to a standard wireless communication network (e.g., CDMA networks provided by companies such as Sprint and Verizon; GSM/GPRS networks provided by ATT and Cingular; or wireless data networks such as the Mobitex or DataTac networks). These networks connect a wireless transmitter or a silicon-based chipset to the Internet-based software piece. Also in the above-described methods, the 'measuring' and 'transmitting' steps can be performed at any time and with any frequency, depending on the diagnoses being performed. The wireless network may also short-range wireless transmitters and receivers. These devices, for example, may use wireless protocols such as any version of (e.g., 802.11b), Bluetooth™, or a short-range radio protocol.

The term 'web page' refers to a standard, single graphical user interface or 'page' that is hosted on the Internet or worldwide web. Web pages typically include: 1) a 'graphical' component for displaying a user interface (typically written in a computer language called 'HTML' or hypertext mark-up language); an 'application' component that produces functional applications, e.g. sorting and customer registration, for the graphical functions on the page (typically written in, e.g., C++ or java); and a database component that accesses a relational database (typically written in a database-specific language, e.g. SQL*Plus for Oracle databases). A 'web site' typically includes multiple web pages, many of which are 'linked' together, that are accessed through a series of 'mouse clicks'.

Different embodiments of the invention include one or more of the following advantages. They allow one or more medical professionals to remotely analyze a large group of patients accurately and in real-time. Patients can measure their vital signs and subsequently have these data monitored by a medical professional located thousands of miles away. Data measured with high frequency (e.g., several times each day) provide a relatively comprehensive data set compared to that measured during medical appointments separated by several weeks or even months. This allows both the patient and medical professional to observe trends in the data, such as a gradual increase or decrease in a particular vital sign, which may indicate a medical condition. And they minimize effects of white coat syndrome since the patient can make measurements at home or work.

Diabetic patients can use at least some of the embodiments to wirelessly transmit their blood glucose level after each measurement, making it unnecessary to record these data in a logbook. Patients with Internet access can view data analyzed with a variety of algorithms. Similarly, parents can remotely view data measured by their children. During medical appointments professionals can view the data and adjust a patient's exercise and diet to better control their diabetes. A call center staffed by medical professionals can use the invention to constantly monitor patients, such as patients with severe cardiac conditions, and quickly respond in the case of emergency.

Ultimately various embodiments of the wireless, internet-based medical-diagnostic system described herein provide an in-depth, cost-effective mechanism to evaluate a patient's medical condition. Certain medical conditions can be controlled, and in some cases predicted, before they actually occur. Moreover, data from the patient can be collected and analyzed, often in a continuous manner, while the patient participates in their normal, day-to-day activities. This provides a relatively comprehensive diagnosis that is not possible using a conventional medical-diagnostic system.

An internet-based software system for medical diagnoses can also be easily updated and made available to a large group of users simply by updating software on the web site. In contrast, a comparable updating process for a series of in-hospital medical devices can only be accomplished by updating the software on each individual device. This, of course, is time-consuming, inefficient, and expensive, and introduces the possibility that many devices within a particular product line will not have the very latest software.

The device used to access and transmit the patient's data can be small, portable, and low-cost. Measurements are made in a matter of minutes and transmitted with a latency of a few seconds. A single device can also be used to measure and transmit data from multiple patients, provided it includes software and hardware that allows each patient to enter an identifying code that is, in turn, associated with their respective vital-sign data.

The resulting data, of course, have many uses for patients, medical professional, insurance companies, pharmaceutical agencies conducting clinical trials, and organizations for home-health monitoring.

These and other advantages of various embodiments of the invention are described in the following detailed disclosure and in the claims.

BRIEF DESCRIPTION OF DRAWINGS

The features and advantages of embodiments of the present invention can be understood by reference to the following detailed description taken with the drawings, in which.

DESCRIPTION OF THE PREFERRED EMBODIMENTS

Figure 1:
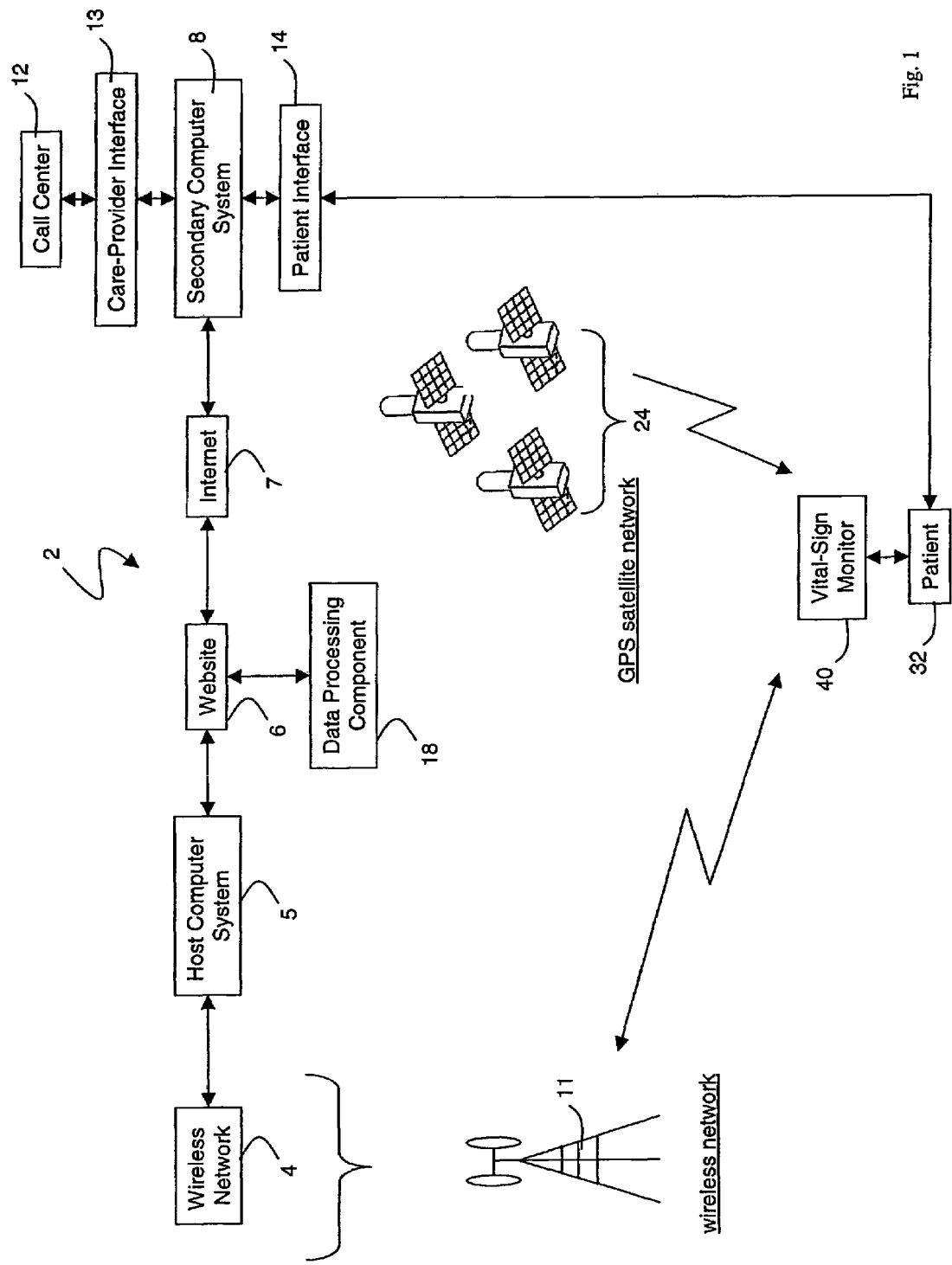
FIG. 1 is a schematic drawing showing an internet-based medical-diagnostic system that transmits vital-sign data through a wireless network to an Internet-accessible host computer system.

FIG. 1 shows a schematic drawing of an Internet-based medical-diagnostic system 2. The system 2 features a vital-signs monitor 40 that measures vital-sign data from a patient 32 and wirelessly transmits these data over a wireless network 4 to a web site 6 accessible through the Internet 7. The system 2 functions in a bi-directional manner, i.e. the vital-sign monitor 40 can both send and receive data. In typical operation, for example, the vital-sign monitor 40 predominantly transmits vital-sign data through the wireless network 4 to the web site 6. Using the same network, the monitor 40 also receives text-based instant messages (described with reference to FIG. 8) and software upgrades to function in a bi-directional manner.

The vital-sign monitor 40 includes systems that measure, e.g., blood pressure, $O_2$ saturation, ECGs, heart rate, respiratory rate, and blood glucose level. After these data are measured, software in the monitor 40 formats them into a data packet. The monitor radiates the packet to a base station 11 included in the wireless network 4. A host computer system 5 running a gateway software piece connects to the wireless network 4 and receives data packet from multiple vital-sign monitors. The host computer system 5, for example, may include multiple computers, software pieces, and other signal-processing and switching equipment, such as routers and digital signal processors. The wireless network 4 typically transfers data to the host computer system 5 using a TCP/IP-based connection, or with a dedicated digital leased line (e.g., a frame-relay circuit or a digital line running an X.25 protocol). The host computer system 5 also hosts the web site 6 using conventional computer hardware (e.g. computer servers for both a database and the web site) and software (e.g., web server and database software).

The patient 32 accesses a patient interface 14 hosted on the web site 6 through the Internet 7 from a secondary computer system 8. The patient interface 14 displays vital-sign data measured from a single patient. A call center 12, typically staffed with medical professionals such as doctors, nurses, or nurse practioners, accesses a care-provider interface 13 hosted on the website 6. The care-provider interface 13 displays vital-sign data from multiple patients. Both the patient and care-provider interfaces are described in more detail with references to FIGS. 4-8.

The vital-sign monitor 40 additionally includes a GPS system that receives GPS signals from a conventional GPS satellite system 24 and processes these signals to determine a location (more specifically the latitude, longitude, and altitude) of the monitor and, presumably, the patient. This location, for example, could be used to locate a patient during an emergency for purposes of dispatching an ambulance.

The appliance transmits separate data packets through the wireless network 11 that feature a 'payload' containing either the vital-sign data or the GPS-determined location. Typically these data are sent in separate packets, although they could be bundled into a single packet. The data packets additionally contain information of the packets' status, an address describing their destination, and an address describing their origin. These data packets are transmitted over conventional wireless network, such as a CDMA, GSM/GPSRS, Mobitex, or DataTac network. The specific network is associated with the wireless transmitter used by the monitor to transmit the data packet.

Figure 2:
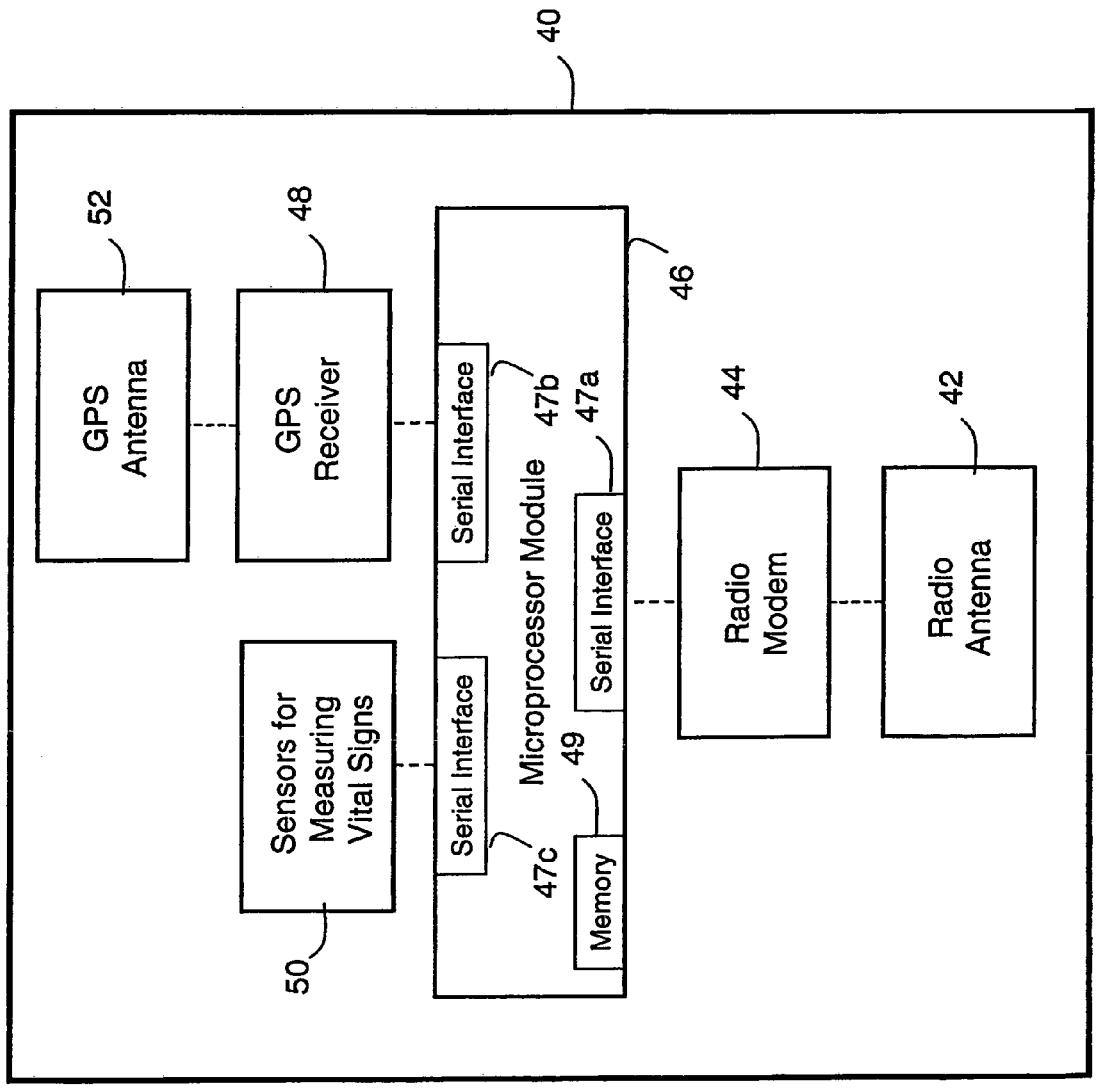
FIG. 2 is a schematic drawing of the medical-diagnostic system of FIG. 1 featuring a vital-sign monitor, a GPS system, and a wireless-transmitting system.

FIG. 2 shows a schematic drawing that describes the vital-sign monitor 40 in more detail. The monitor features a microprocessor module 46 that includes a computer microprocessor or microcontroller and multiple serial interfaces 47a-c. The microprocessor module communicates with external devices using, for example, an RS-232 or other serial protocol operating over the serial interfaces 47a-c. One serial interface 47c communicates with the sensors for monitoring vital signs 50 described in more detail with reference to FIG. 3. Through this serial interface the microprocessor module 46 collects vital-sign data and formats it into a packet as described above.

The microprocessor module 46 collects GPS location-based data from a GPS receiver 48 through a second serial interface 47b, also communicating with an RS-232 or other serial protocol. The GPS receiver 48 generates the location-based data by collecting GPS signals from orbiting GPS satellites using a GPS antenna 52. Both the GPS receiver 48 and the sensors for measuring vital signs 50 may continually and automatically send data across the respective serial ports 47b, 47c at a well-defined frequency (e.g., every second). Or they may only send data in response to a command sent by the microprocessor module 46.

Once the microprocessor module 46 collects vital-sign and location-based data, these data are formatted into separate packets and transmitting through a third serial interface 47a to a radio modem 44. The radio modem 44 functions as a wireless transmitter that transmits data packets through an antenna 42 and over a wireless network. As described above, the wireless network chosen to transmit the data packets will dictate the type of wireless transmitter used in the monitor 40.

The microprocessor module 46 runs software and a data-collection 'schema' loaded into memory 49, such as a random-access memory. The schema is essentially a 'map' that describes: i) the type of data collected from the sensors for monitoring vital signs 50 and the GPS receiver 48; ii) the frequency that these data are collected; and iii) the frequency that these data are transmitted. A schema specific to a given set of sensors is typically loaded onto the memory 49 before the monitor is distributed to a patient. During operation, the vital-sign monitor collects vital-sign and location-based data defined by the schema, and transmits these data in packets as described above. The network transfers the data packet to the host computer system. There, the host computer system analyzes the data packet using a 'map' that corresponds to the schema to generate a data set. Every schema has a corresponding map. The map includes, for example, a list of the collected data, and an acronym and unit for each datum. The data set, acronym, and units are then displayed on the web site and are viewed by any 'registered' user (i.e., a patient or call center employee with a username and corresponding password) with Internet connectivity.

Figure 3:
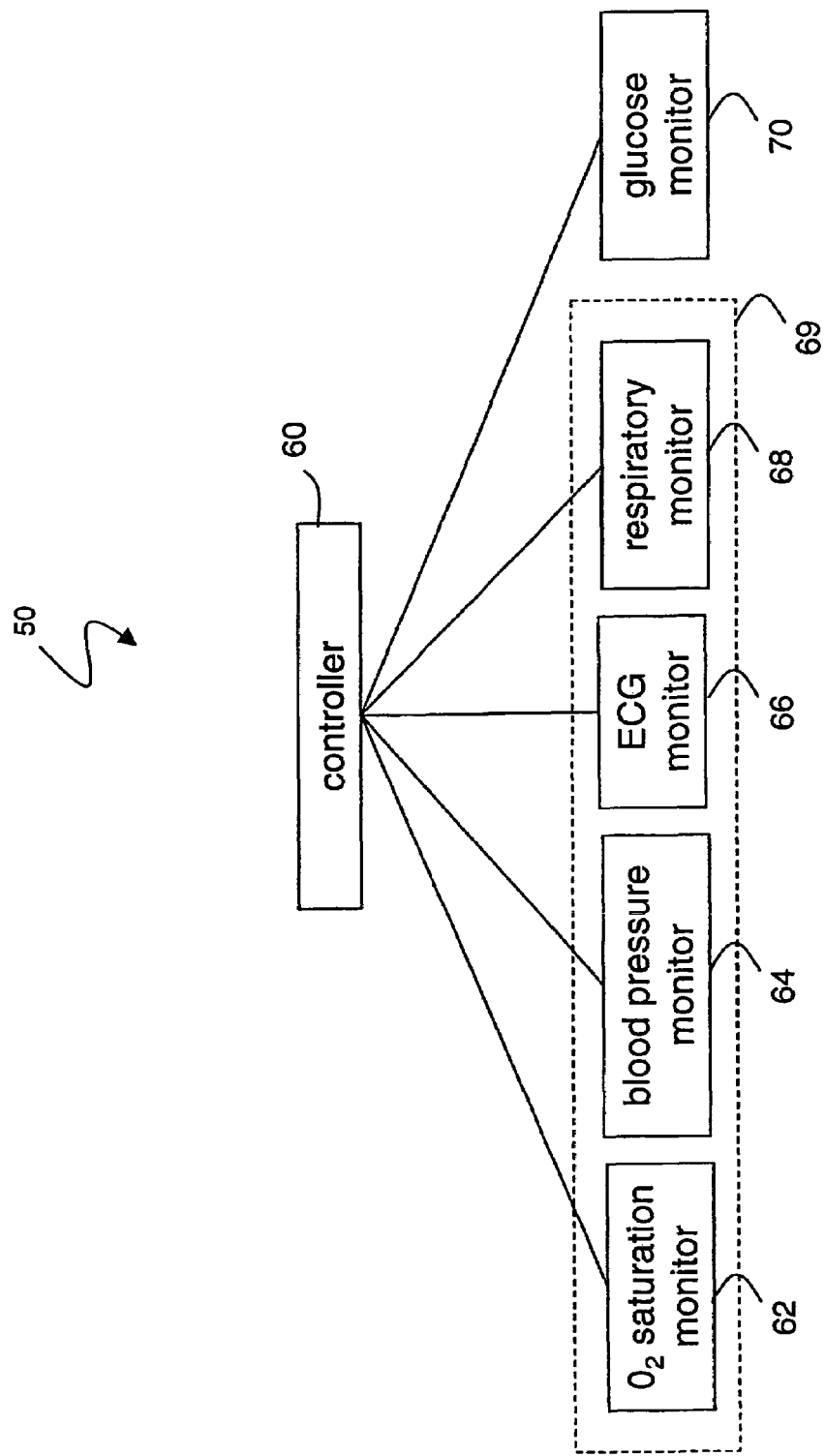
FIG. 3 is a schematic drawing of the vital-sign monitor featured in the medical-diagnostic system of FIG. 2.

FIG. 3 shows the sensors for monitoring vital signs 50 in more detail. The sensors 50 feature a controller 60, such as a separate microprocessor or microcontroller, that interfaces to monitors for: i) $O_2$ saturation 62; blood pressure 64; ECG 66; and respiratory rate 68. Each of these monitors is typically included in a single medical device 69 similar to that currently used in hospitals to characterize a patient's vital signs. In addition, the controller 60 communicates with a glucometer 70 using the same microprocessor or microcontroller. Typically the monitor includes a socket or plug to which the glucometer 70 connects. This way, a diabetic patient can carry and use the glucometer (which is typically portable) during day-to-day activities, and then attach this device to the monitor 40 at the end of the day. In contrast, the medical device 69 including the above-mentioned monitors is typically larger than a conventional glucometer, and is thus connected directly to the controller 60 at all times. Companies manufacturing medical devices including the monitors described in FIG. 3 include the following: Smith-BCI, Welch Allyn, Medtronic, Hewlett Packard, and Philips Medical. Similarly, companies manufacturing glucometers that may be used with the vital-sign monitor include Johnson & Johnson, Bayer and Roche.

Figure 4:
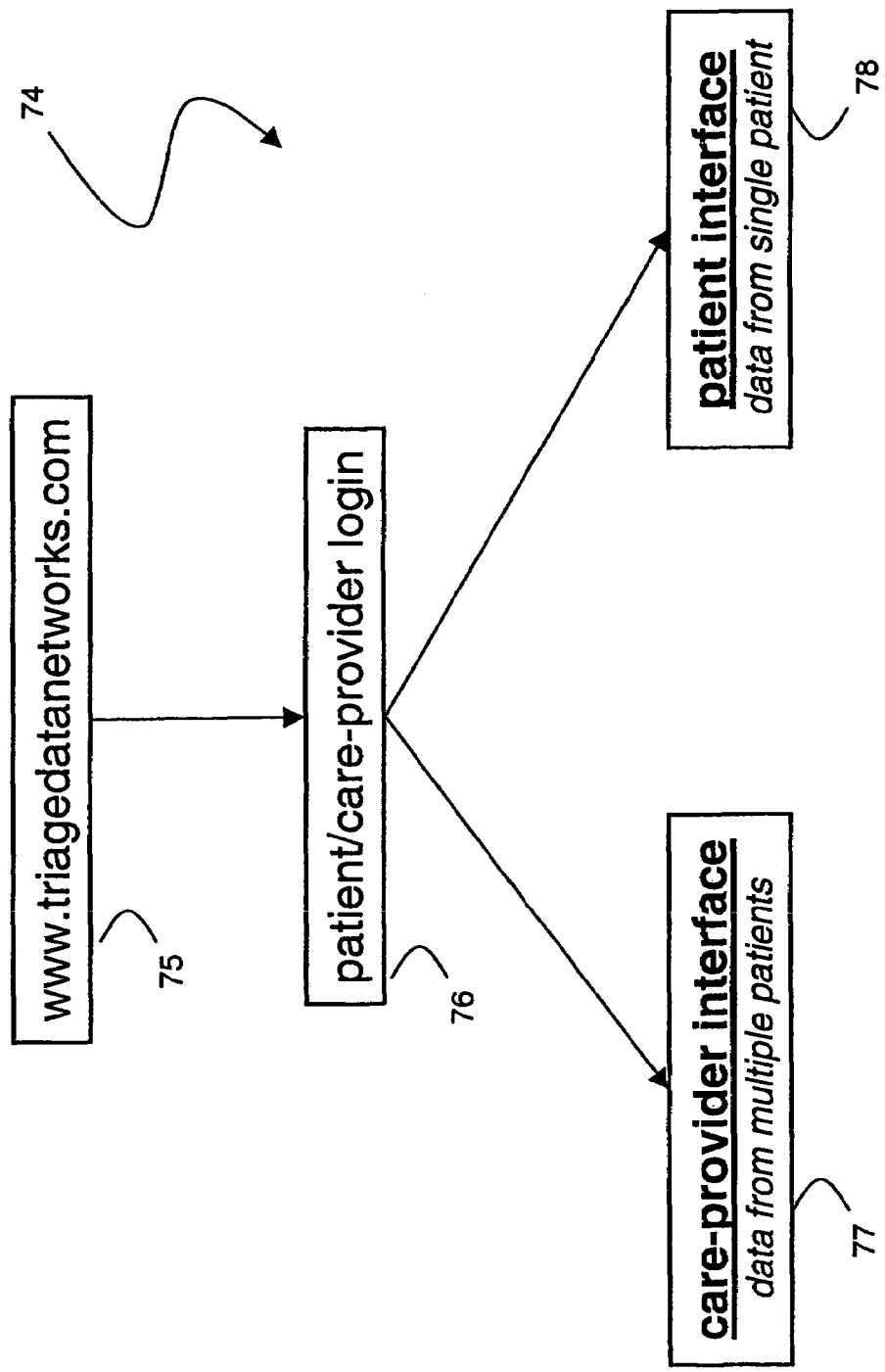
FIG. 4 is a schematic drawing of a web site that displays data from the medical-diagnostic system of FIG. 1 and features web pages associated with either a care-provider or patient interface.

FIG. 4 illustrates the concept of patient and care-provider interfaces in more detail. The figure shows a schematic drawing of a login process 74 for a web site 75 that displays vital-sign data for a series of 'patients' associated with a single 'care provider'. Each patient is associated with a single vital-sign monitor. A user 'logs' into the web site 75 through a login interface 76 by entering a username and password that, once entered, are compared to a database associated with the web site. The comparison determines if the user is a patient or a care provider. If the user is determined to be a care provider, the web site renders a care-provider interface 77 that contains multiple web pages describing, e.g., vital-sign and location-based data for each patient associated, e.g., with a given hospital. Users viewing the care-provider interface 77 do not have access to data corresponding to patients associated with another care provider. If the user is determined to be a patient, the web site 75 renders a patient interface 78 that contains vital-sign and location-based data for the patient. Each patient using the web site 75 is associated with a unique patient interface 78 that renders following a login event. Note that patients sharing a single vital-sign monitor will only have access to their personal patient interface. In this case, the patient using the monitor needs to enter a code (e.g., an alphanumeric code) to log into the monitor. This code is then transmitted with the vital-sign and GPS-determined data. The host computer system processes the code to route these data to a section of the database corresponding specifically to the patient using the monitor.

Figure 5:
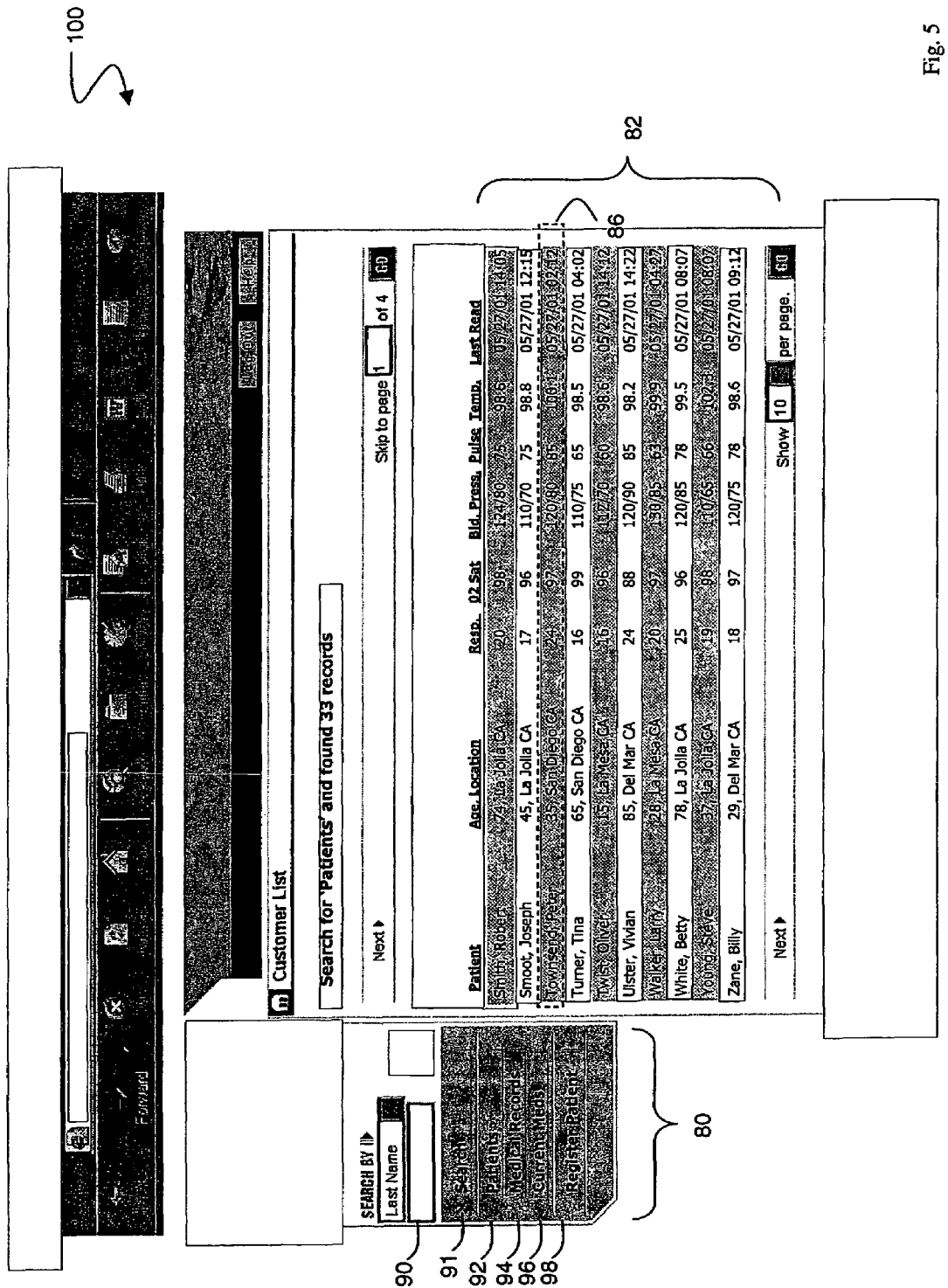
FIG. 5 is a screen capture of a web page from the care-provider interface of FIG. 4 that shows a list of patients, each corresponding to a single care-provider, and their associated vital-sign data.

FIG. 5 shows a screen capture of a web page 100 included in the care-provider interface referred to in FIG. 4. The web page 100 features a left-hand navigation bar 80 and a table 82 that lists vital-sign data for a group of patients associated with the call center. The table 82 includes unique fields for the patient's name, the age and location, and vital-sign medical data including: respiratory rate, $O_2$ saturation, blood pressure, pulse rate, and temperature. The table also includes a field listing a time when the patient's data was last collected. As an example, the table 82 includes a row 86 corresponding to a 35-year-old patient named Peter Townsend from San Diego, Calif. The patient's last reading, measured at 2:12 on May 27, 2001, yields the following vital-sign data:

| | |
|---|---|
| respiratory rate: | 20 breaths/minute |
| $O_2$ saturation: | 97% |
| blood Pressure: | 120 mm Hg/80 mm Hg |
| pulse rate: | 85 beats/minute |
| temperature: | 100.1° F. |

According to the method described above, a call-center operator monitors these data by accessing the web page 100 through the Internet. After analyzing the data, the operator can use the web page 100 to access other data corresponding to the patient, such as their current medication using button 98, or their medical records using button 94. The operator can also search for a particular patient by entering their last name in a search field 90 and then clicking a 'Search' button 91. Or the operator can register a new patient by clicking on a 'Register Patient' button 98 included in the left-hand navigation bar 80.

The call-center operator diagnoses the patient using the vital-sign data in a manner similar to protocols used during a conventional medical appointment. By using the above-described method, however, the operator can efficiently monitor hundreds of patients, each in a remote location, through the Internet. For example, following analysis, the operator may send the patient to a hospital, or may recommend a therapy to the patient using a telephone, email, or Internet-based instant message. Or if the patient's data looks normal the operator may deem the patient healthy and issue a clean bill of health.

Figure 6:
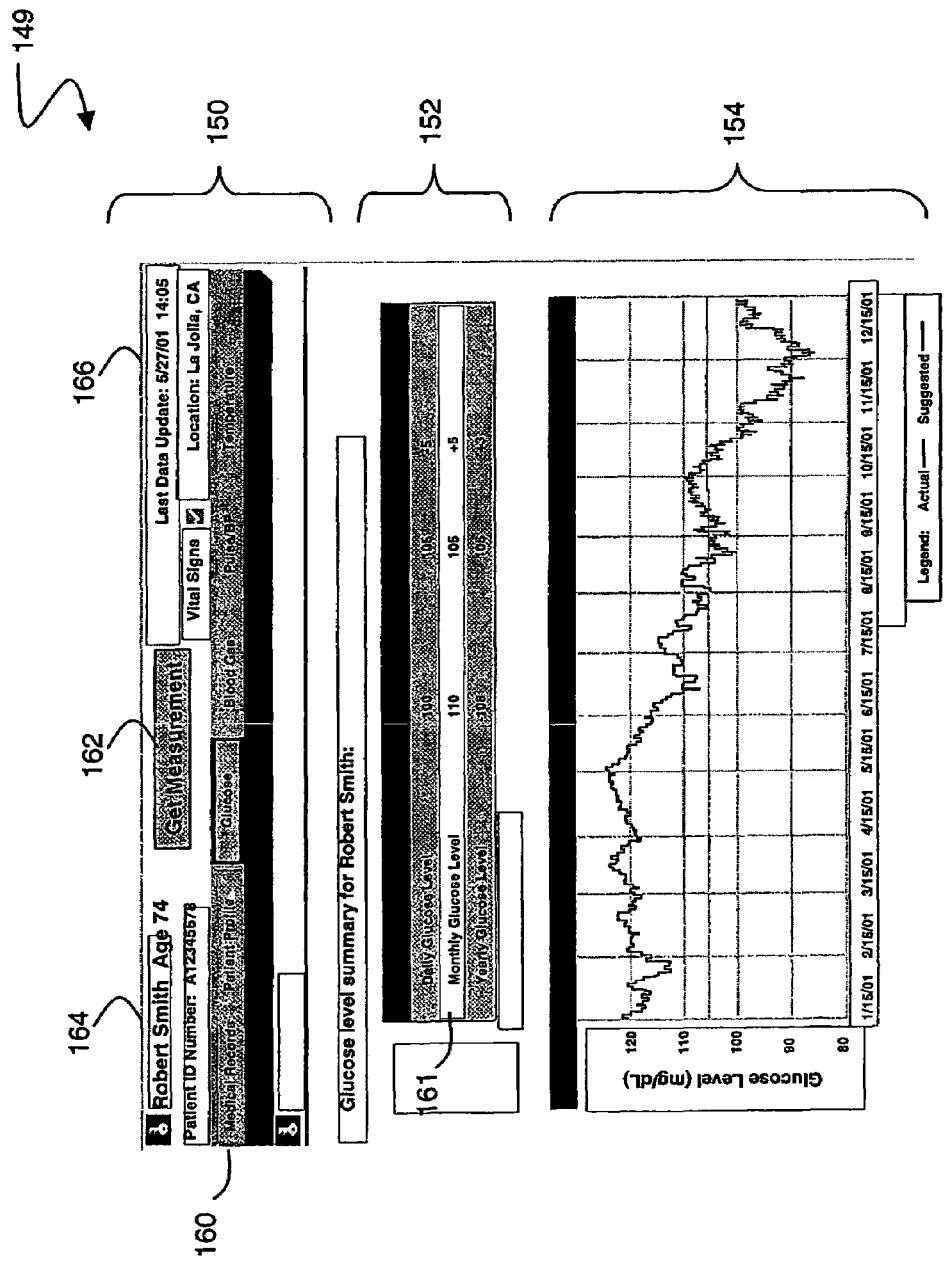
FIG. 6 is a screen capture of a web page from the care-provider interface of FIG. 5 that features a plot of a patient's time-dependent blood glucose level.

Both the care-provider and patient interfaces may additionally include comprehensive displays of the patient's time-dependent vital-sign data. FIG. 6, for example, shows a web page 149 that includes a header field 150 that lists general information about the patient and recent measurements, a table 152 that lists measured vital signs and suggested values of the vital signs, and a graph 154 that plots the vital-sign data in a time-dependent manner. The header field 150 includes fields for the patient's name 164, a time/date stamp 166 corresponding to the time and GPS-determined location of the last reading, and a 'Get Measurement' button 162 that if clicked remotely initiates a measurement by wirelessly sending a command to the vital-sign monitor. This command could: i) prompt the patient to make a new measurement; ii) automatically initiate a measurement if the vital-sign monitor is attached to the patient; or iii) retrieve vital-sign data stored in the monitor's memory. The header field also includes a series of tabs 160 that each list tables and graphs corresponding to a different vital sign.

For example, the web page 149 shown in FIG. 5 shows data corresponding to a patient's glucose level as measured with a glucometer and wirelessly transmitted as described above. The table 152 lists a series of data fields 161 that show running average values of the patient's daily, monthly, and yearly glucose levels. The levels are compared to a series of corresponding 'suggested' values that are extracted from a database associated with the web site. The table then calculates the difference between the running average and suggested values to give the patient an idea of how their data compares to that of a healthy patient.

The graph 154 shows a simple plot of the patient's glucose level vs. a time/date stamp corresponding to a particular measurement. These time-dependent data are then compared to the same suggested values (in this case 105 mg/dL) of glucose listed in the table 152. The graph 154 shows both the patient and call-center operator trends in the glucose level. These trends, for example, may be used to adjust the patient's diet, exercise level, or insulin dosage.

Figure 7:
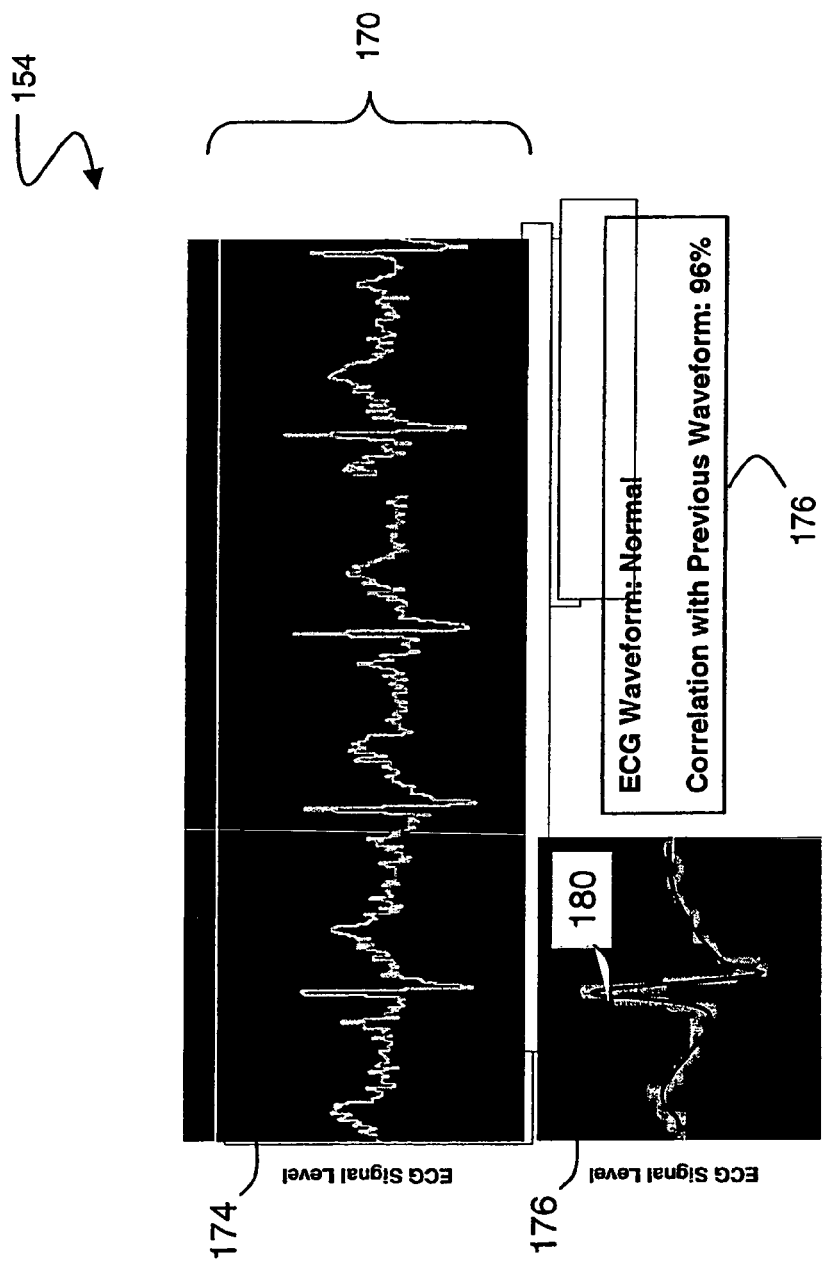
FIG. 7 is a screen capture of a portion of a web page from the care-provider interface of FIG. 5 that features an ECG and a mathematical function used to model the ECG.

FIG. 7 shows another example of how vital-sign data measured from the patient and wirelessly transmitted through the wireless network to the Internet can be analyzed in a graphical form. In this case, the web page 154 shows a graph 170 of an ECG waveform 174 measured from the patient. The waveform 174 features a series of cardiac rhythms, shown in more detail in a window 176 on the web page, that indicate how the patient's heart is beating. The cardiac rhythms are measured by electrodes attached to the patient, and typically represent electrical measurements made at a frequency of approximately 100 to 120 samples/second. To display these data, the wireless medical device transmits a single packet containing a few seconds worth of data (i.e. a few hundred samples). Or the device may transmit several packets, each containing fewer samples. In this case the computer used by the web site for data analysis parses the packets and pieces together the data from the individual packets to form a single waveform. As shown in the window 176, the computer can also analyze a portion of the waveform by comparing it to a mathematical function (using, e.g., a least-squares 'fitting' algorithm), represented by a curve 180. The mathematical function, for example, may be used to analyze the ECG waveform in a more quantitative manner. For example, as shown in a table 176, the mathematical parameters used to generate the curve 180 may be compared to those used to generate a curve for analyzing a previous ECG waveform. This comparison yields a quantitative correlation to the earlier waveform, thereby allowing both the patient and the call-center operator to gauge the patient's time-dependent cardiac behavior. This comparison can also determine if the patient's cardiac response is normal or abnormal, as shown in the table 176.

Figure 8:
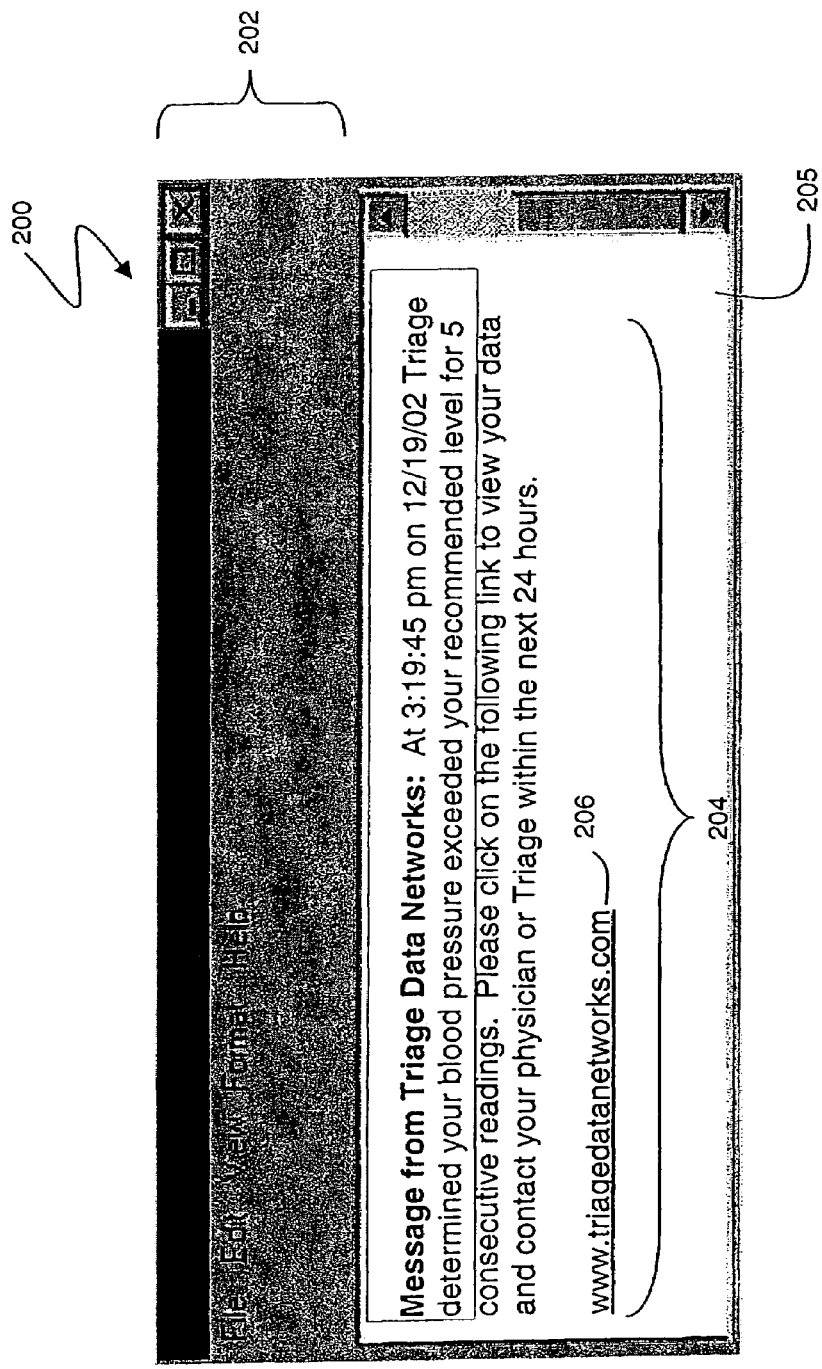
FIG. 8 is a screen capture from an Internet-based instant message transmitted by the medical-diagnostic system of FIG. 1.

Using the above-described system, following analysis of the vital-sign data a call-center operator may contact a patient to describe a potential medical problem. The operator may use a conventional telephone, or an Internet-based contact method such as an email or instant message. FIG. 8, for example, shows a screen capture of an instant message 200 transmitted from the call center to the patient's vital-sign monitor. Such an instant message 200 can be sent using a conventional instant message software program, such as that supplied by Yahoo™ or America OnLine™. The instant message can be sent to the patient's computer, cellular telephone, personal digital assistant, or a comparable device. It includes a header portion 202 that lists options for storing, editing, viewing, and formatting the message. And the message 200 features a text window 205 that lists a text message 204 sent from the call-center operator to the patient. The text message 204 also includes an Internet link 206 to the patient's web page that, when clicked, displays the pages described in FIGS. 4-7 above.

Other embodiments are also within the scope of the invention. In particular, the web pages used to display the data can take many different forms, as can the manner in which the data are displayed. Web pages are typically written in a computer language such as 'HTML' (hypertext mark-up language), and may also contain computer code written in languages such as java and javascript for performing certain functions (e.g., sorting of names). The web pages are also associated with database software (provided by companies such as Oracle and Microsoft) that is used to store and access data. Equivalent versions of these computer languages and software can also be used. In general, the graphical content and functionality of the web pages may vary substantially from what is shown in the above-described figures. In addition, web pages may also be formatted using standard wireless access protocols (WAP) so that they can be accessed using wireless devices such as cellular telephones, personal digital assistants (PDAs), and related devices.

Different web pages may be designed and accessed depending on the end-user. As described above, individual users have access to web pages that only their vital-sign data (i.e., the patient interface), while organizations that support a large number of patients (e.g. hospitals) have access to web pages that contain data from a group of patients (i.e., the care-provider interface). Other interfaces can also be used with the web site, such as interfaces used for: insurance companies, members of a particular company, clinical trials for pharmaceutical companies, and e-commerce purposes. Vital-sign data displayed on these web pages, for example, can be sorted and analyzed depending on the patient's medical history, age, sex, medical condition, and geographic location.

The web pages also support a wide range of algorithms that can be used to analyze data once it is extracted from the data packets. For example, the above-mentioned instant message or email can be sent out as an 'alert' in response to vitals signs indicating a medical condition that requires immediate attention. Alternatively, the message could be sent out when a data parameter (e.g. temperature) exceeded a predetermined value. In some cases, multiple parameters (e.g., $O_2$ saturation, ECG waveform) can be analyzed simultaneously to generate an alert message. In general, an alert message can be sent out after analyzing one or more data parameters using any type of algorithm. These algorithms range from the relatively simple (e.g., comparing blood pressure to a recommended value) to the complex (e.g., predictive medical diagnoses using 'data mining' techniques). In some cases data may be 'fit' using algorithms such as a linear or non-linear least-squares fitting algorithm. In general, any algorithm that processes data collected with the above-described method is within the scope of the invention.

In other embodiments, additional hardware can be added to the medical device to modify its performance. For example, the radio modem used to transmit the data may employ a terrestrial GPS system, such as that available on modems designed by Qualcomm, Inc. In general, the wireless transmitter and general system described above can be used to transmit data generated with any medical device, including devices that measure or characterize cholesterol, coumadin levels, clotting factors, proteins or antibodies, illegal substances, or levels pharmaceutical compounds.

In certain embodiments, the wireless transmitter transmits blood pressure, heart rate, and $O_2$ saturation information determined from a hand or finger-worn monitor. The blood pressure information may be determined from a finger-worn monitor that measures $O_2$ saturation. In other embodiments, the monitor can be used to characterize a wide range of maladies, such as diabetes, congestive heart failure, sleep apnea and other sleep disorders, asthma, heart attack and other cardiac conditions, stroke, Alzheimer's disease, and hypertension.

In still other embodiments, the vital-sign monitor or components thereof and GPS electronics are integrated into other devices to perform the above-described measurements. For example, in one embodiment, the sensor for the pulse oximeter makes a measurement from the patient's earlobe and is integrated into a head-worn unit, e.g. a pair of eyeglasses or sunglasses. In this case, electronics that analyze the signals generated from the sensor can also be integrated into the head-worn unit (e.g., into the frames of the eyeglasses) or into a belt-worn module that, in turn, is attached to the head-worn unit using a wired or unwired (e.g., short-range wireless) connection. The belt-worn unit includes a controller and serial port that, respectively, analyze the data and download the data to an external computer. A display (e.g., a 'head's up' or holographic display) for displaying the vital-sign measurements can be integrated into the head-worn unit, e.g. into the transparent glass portion of the eyeglasses. In this way, for example, a patient can monitor his real-time vital signs during exercise or everyday activities. Alternatively, a text-to-speech controller can be used to describe the data in an audio manner to the patient.

The head-worn embodiment of the vital-sign monitor can also include memory that stores the measured vital signs and a GPS-determined location. This way, the location and vital-sign data can be downloaded to a computer through the serial port and viewed by the patient. This allows, for example, a patient to monitor his vital signs as a function of location or time. Such a device would be particularly useful for training purposes for athletes, e.g. marathon runners.

In a related embodiment, the sensor for the pulse oximeter takes the form of a finger ring or an adhesive patch and is connected to the belt-worn module as described above. The connection can be a wired or unwired connection.

Still other embodiments are within the scope of the following claims.

What is claimed is:

1. A system for monitoring a patient, comprising:
    a vital-sign monitor comprising a sensor for measuring data characterizing $O_2$ saturation from the patient;
    a global positioning system for determining location-based data;
    a wireless transmitter configured to receive the data and wirelessly transmit these data through a wireless network;
    a gateway software piece that receives and processes the data from the wireless network;
    a database software piece that communicates with the gateway software piece to receive the data and store them in a computer memory; and
    an Internet-based user interface that displays the data and comprises a first interface that displays vital-sign and location-based data for a single patient and a second interface that displays vital-sign and location-based data for a plurality of patients.

2. A system for monitoring a patient, comprising:
    a vital-sign monitor comprising:
    sensors for measuring from the patient at least one of the following vital-sign data: $O_2$ saturation, blood pressure, heart rate, electro-cardiogram, respiratory rate, temperature and blood glucose level;
    a global positioning system that generates location-based data; and
    a wireless component that transmits the vital-sign and location-based data and receives component code;
    a wireless transmitter configured to receive the vital-sign and location-based data and wirelessly transmit these data through a wireless network;
    a gateway software piece that receives and processes the vital-sign and location-based data from the wireless network;
    a database software piece that communicates with the gateway software piece to receive the vital-sign and location-based data and stores them in a computer memory; and
    an Internet-based user interface that displays the vital sign and location-based data and comprises a first interface that displays vital-sign and location-based data for a single patient and a second interface that displays vital sign and location-based data for a plurality of patients.

3. The system of claim 2, wherein the Internet-based user interface comprises a login functionality that analyzes input information and in response renders either a first or second interface.

4. The system of claim 3, wherein the first interface is associated with a single entity, and the second interface is associated with a group of entities.

5. The system of claim 3, wherein the input information comprises a user login and a password.

6. The system of claim 3, wherein the second interface comprises a numerical table that displays the vital-sign and location-based data associated with the plurality of patients.

7. The system of claim 2, wherein the second interface comprises a web page that displays an alert message associated with a patient.

8. The system of claim 7, further comprising an application software piece that processes vital-sign data to generate the alert message.

9. The system of claim 8, wherein the application software piece comprises an algorithm that compares vital-sign data to a pre-determined level to generate the alert message.

10. The system of claim 7, further comprising an application software piece configured to process multiple vital-sign data to generate the alert message.

11. The system of claim 10, wherein the application software piece processes vital-sign data and a patient's age to generate the alert message.

12. The system of claim 10, wherein the application software piece processes vital-sign data and a patient's gender to generate the alert message.

13. The system of claim 3, wherein the system further comprises a first software component that transmits an electronic file.

14. The system of claim 13, wherein the vital-sign monitor further comprises a second software component that receives the electronic file.

15. The system of claim 14, wherein the Internet-based user interface comprises a web page that sends an email or electronic message to a patient.

16. The system of claim 15, wherein the email or electronic message is a pre-determined message stored in the computer memory.

17. The system of claim 15, wherein the system automatically transmits the email or electronic message following analysis of the vital-sign and location-based data.

18. The system of claim 15, wherein the system automatically transmits a report.

19. The system of claim 18, wherein the database software piece is configured to generate the report.

20. The system of claim 14, wherein the vital-sign monitor further comprises a display that displays an email or electronic message received from the Internet.

21. The system of claim 14, wherein the second software component is configured to receive wirelessly transmitted computer code.

22. The system of claim 21, wherein the second software component processes the wirelessly transmitted computer code to update an existing computer code in the vital-sign monitor.

23. The system of claim 22, wherein the second software component processes the wirelessly transmitted computer code to load a schema into the vital-sign monitor.

24. The system of claim 23, wherein the second software component processes the wirelessly transmitted computer code to modify the vital-sign monitor's transmission properties.

25. The system of claim 24, where the second software component processes the wirelessly transmitted computer code to modify the vital-sign monitor's transmission frequency.

26. The system of claim 23, wherein the second software component processes the wirelessly transmitted computer code to modify the data transmitted by the vital-sign monitor.

27. The system of claim 13, wherein the first software component is configured to transmit data formatted in an XML-based format.

28. The system of claim 27, wherein the XML-based format is compatible with a second Internet-based software system.

* * * * *